United States Patent
Walsh et al.

(10) Patent No.: US 11,740,148 B2
(45) Date of Patent: *Aug. 29, 2023

(54) INTEGRATED SENSOR TO MONITOR FLUID DELIVERY

(71) Applicant: CareFusion 303, Inc., San Diego, CA (US)

(72) Inventors: Timothy Adam Walsh, Andover, MA (US); Christian Sandmann, Wayne, NJ (US)

(73) Assignee: CAREFUSION 303, INC., San Diego, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 17/021,694

(22) Filed: Sep. 15, 2020

(65) Prior Publication Data

US 2020/0408628 A1 Dec. 31, 2020

Related U.S. Application Data

(63) Continuation of application No. 15/896,375, filed on Feb. 14, 2018, now Pat. No. 10,809,139.

(51) Int. Cl.
*G01L 9/00* (2006.01)
*B81B 3/00* (2006.01)
(Continued)

(52) U.S. Cl.
CPC ....... *G01L 9/0022* (2013.01); *A61M 5/16854* (2013.01); *A61M 5/16877* (2013.01);
(Continued)

(58) Field of Classification Search
CPC ........... H01L 41/1138; A61M 5/16877; A61M 5/16854; A61M 5/16886; A61M 5/172;
(Continued)

(56) References Cited

U.S. PATENT DOCUMENTS 3,820,392 A 6/1974 Beck et al.
3,893,228 A 7/1975 George et al.
(Continued)

FOREIGN PATENT DOCUMENTS

AU 4117572 A 10/1973
CN 103791236 A 5/2014
(Continued)

OTHER PUBLICATIONS

International Search Report and Written Opinion for Application No. PCT/US2019/017699, dated May 9, 2019, 17 pages.
(Continued)

*Primary Examiner* — Helen C Kwok
(74) *Attorney, Agent, or Firm* — Morgan, Lewis & Bockius LLP

(57) ABSTRACT

A sensor for use in a fluid flow application is provided. The sensor includes an inlet chamber configured to receive a fluid flow from a first conduit, an outlet chamber configured to provide the fluid flow to a second conduit, and a membrane separating the inlet chamber from the outlet chamber, the membrane including a fluid passage to allow the fluid flow from the inlet chamber to the outlet chamber. The sensor also includes a circuit component disposed on the membrane, having an electrical property configured to change according to a deformation of the membrane, and a conductor formed on a substrate and coupled with the circuit component, to provide an electrical signal based on a change in the electrical property of the circuit component. The membrane includes an epitaxial layer formed on the substrate. Methods for fabricating and using the above sensor are also presented.

16 Claims, 9 Drawing Sheets

(51) Int. Cl.
*A61M 5/168* (2006.01)
*A61M 5/172* (2006.01)
*C30B 29/06* (2006.01)
*H10N 30/30* (2023.01)

(52) U.S. Cl.
CPC ........ *A61M 5/16886* (2013.01); *A61M 5/172* (2013.01); *B81B 3/0021* (2013.01); *C30B 29/06* (2013.01); *H10N 30/308* (2023.02); *A61M 2205/3331* (2013.01); *A61M 2205/3334* (2013.01); *A61M 2205/3368* (2013.01); *B81B 2201/0264* (2013.01); *B81B 2201/05* (2013.01)

(58) Field of Classification Search
CPC ......... G01F 1/28; G01F 1/7084; G01G 1/708; G01L 9/0022
See application file for complete search history.

(56) References Cited

U.S. PATENT DOCUMENTS

| | | | |
|---|---|---|---|
| 4,222,277 A | | 9/1980 | Kurtz et al. |
| 4,275,406 A | | 6/1981 | Muller et al. |
| 4,395,915 A | | 8/1983 | Singh |
| 5,062,302 A | | 11/1991 | Petersen et al. |
| 5,375,473 A | * | 12/1994 | Ikeda ................. G01L 19/0618 73/706 |
| 5,395,802 A | * | 3/1995 | Kiyota ................ B81C 1/00595 438/924 |
| 5,485,753 A | | 1/1996 | Burns et al. |
| 5,490,034 A | | 2/1996 | Zavracky et al. |
| 5,511,428 A | | 4/1996 | Goldberg et al. |
| 5,515,735 A | | 5/1996 | Sarihan |
| 5,581,028 A | * | 12/1996 | Barth ..................... G01F 15/00 73/204.26 |
| 5,659,138 A | * | 8/1997 | Iwata .................. B81C 1/00047 73/514.33 |
| 5,663,508 A | * | 9/1997 | Sparks ...................... G01P 5/04 73/861.74 |
| 6,023,978 A | | 2/2000 | Dauenhauer et al. |
| 6,150,681 A | | 11/2000 | Allen |
| 6,420,201 B1 | * | 7/2002 | Webster ................. H01L 24/97 438/126 |
| 6,932,893 B2 | | 8/2005 | Bech et al. |
| 6,984,977 B2 | | 1/2006 | Wellstood et al. |
| 8,186,226 B2 | | 5/2012 | Ricks |
| 8,258,450 B1 | | 9/2012 | Fries |
| 8,770,034 B2 | | 7/2014 | Bentley et al. |
| 10,809,139 B2 | * | 10/2020 | Walsh ................. A61M 5/16877 |
| 2002/0003274 A1 | * | 1/2002 | Bryzek ................. G01L 9/0054 257/414 |
| 2003/0061889 A1 | | 4/2003 | Tadigadapa et al. |
| 2003/0116813 A1 | | 6/2003 | Benzel et al. |
| 2004/0163476 A1 | | 8/2004 | Partridge et al. |
| 2005/0199973 A1 | * | 9/2005 | Benzel ................. G01L 9/0042 257/419 |
| 2006/0144152 A1 | | 7/2006 | Cabuz et al. |
| 2006/0258038 A1 | * | 11/2006 | Rich ..................... G01P 15/123 438/52 |
| 2007/0164379 A1 | * | 7/2007 | Brown ................ B81C 1/00666 438/770 |
| 2009/0288497 A1 | * | 11/2009 | Ziegler ............. A61M 5/16854 73/861.61 |
| 2011/0132480 A1 | * | 6/2011 | Chappel ................ A61M 37/00 137/599.06 |
| 2013/0055821 A1 | | 3/2013 | Bentley et al. |
| 2013/0105923 A1 | | 5/2013 | Yu et al. |
| 2013/0228022 A1 | * | 9/2013 | Brown ................. G01L 9/0054 73/862.68 |
| 2014/0113828 A1 | | 4/2014 | Gilbert et al. |
| 2014/0116110 A1 | | 5/2014 | Katase |
| 2014/0298913 A1 | | 10/2014 | Stewart et al. |
| 2015/0297341 A1 | | 10/2015 | Noroozi et al. |
| 2016/0146685 A1 | * | 5/2016 | Chiou ..................... B81B 3/007 73/727 |
| 2016/0176702 A1 | | 6/2016 | Pagani et al. |
| 2016/0339431 A1 | | 11/2016 | Shmilovich et al. |
| 2017/0254713 A1 | * | 9/2017 | Liu ..................... G01L 19/0084 |
| 2018/0024021 A1 | | 1/2018 | Stewart |
| 2019/0127219 A1 | * | 5/2019 | Bengali ............... B81C 1/00071 |

FOREIGN PATENT DOCUMENTS

| | | |
|---|---|---|
| CN | 104771806 A | 7/2014 |
| CN | 203710470 U | 7/2014 |
| CN | 105424261 A | 3/2016 |
| JP | 2017161401 A | 9/2017 |
| WO | WO-2016030836 | 3/2016 |
| WO | WO-2018017134 A1 | 1/2018 |

OTHER PUBLICATIONS

Chinese Office Action for Application No. 201980012186.5, dated Jan. 29, 2022, 23 pages including machine translation.
Chinese Office Action for Application No. 201980013186.5, dated Sep. 27, 2022, 21 pages including translation.
Japanese Office Action for Application No. 2020-543332, dated Oct. 4, 2022, 7 pages including translation.
Canadian Office Action for Application No. 3090897, dated Mar. 28, 2023, 3 pages.
Chinese Office Action for Application No. 201980013186.5, dated Mar. 22, 2023, 24 pages including translation.

* cited by examiner

INTEGRATED SENSOR TO MONITOR FLUID DELIVERY

CROSS-REFERENCE TO RELATED APPLICATION

This application is a continuation of U.S. patent application Ser. No. 15/896,375, filed Feb. 14, 2018, which issued as U.S. Pat. No. 10,809,139 on Oct. 20, 2020, entitled, "INTEGRATED SENSOR TO MONITOR FLUID DELIVERY," which is hereby incorporated by reference in its entirety for all purposes.

BACKGROUND

The present disclosure is generally related to apparatus and methods for fluid flow measurement and control. More specifically, the present disclosure relates to an apparatus and methods to measure fluid flow parameters using microelectromechanical moving systems (MEMS) in fluid delivery applications.

Many approaches to fluid delivery involve measurement of multiple fluid flow parameters that are of relevance for fluid flow control. Some of these parameters are particularly relevant in the case of medical applications (e.g., intravascular drug delivery, subcutaneous drug delivery, and the like). In addition to measuring multiple parameters, it is desirable to provide a compact form factor for ease of handling, and to facilitate movement and access to the device (e.g., healthcare providers, the patient, etc. in medical applications). Typically devices that measure multiple fluid parameters are not compact, and include moving parts that hinder their use in applications where ease of access is desirable (e.g., an emergency room in a healthcare facility, and the like).

SUMMARY

In one or more embodiments a method for making a sensor is presented. The method includes growing an epitaxial layer over a substrate, wherein forming the epitaxial layer comprises selectively implanting a dopant atom to form an electrical component sensitive to a strain in the epitaxial layer, and forming a membrane on the epitaxial layer, the membrane having a thickness selected so that a pressure difference between opposite sides of the membrane induces the strain in the epitaxial layer. The method also includes forming a fluid passage through the membrane, attaching an inlet fitting on the first side of the substrate to form an inlet chamber on a first side of the membrane, attaching an outlet fitting to a second side of the substrate to form an outlet chamber on a second side of the membrane, and bonding an electrical connector to the electrical component.

BRIEF DESCRIPTION OF THE DRAWINGS

In the figures, elements having the same or similar reference numeral have the same or similar functionality or configuration, unless expressly stated otherwise.

DETAILED DESCRIPTION

The disclosure is a monolithically integrated sensor to monitor five parameters during an IV fluid delivery. Some embodiments include sensing modalities such as fluid flow rate, fluid pressure (gauge pressure relative to ambient atmosphere), fluid conductivity, temperature, and presence of air bubbles, among others. Embodiments consistent with the present disclosure include the integration of one or more the above sensing modalities into a single device, and a method to fabricate the device.

Some of the advantages of embodiments consistent with the present disclosure include the combination of different sensing modalities into a small form factor, monolithic package. Also, embodiments as disclosed herein provide a low-cost, high volume manufacturing method for producing the device.

Embodiments disclosed herein may include applications for fluid sensors in intravascular drug delivery. More generally, embodiments consistent with the present disclosure may include applications for fluid systems in subcutaneous fluid delivery for medical applications, or in an implanted system that may directly deliver a fluid to an organ, tumor, and the like, for compounding, removal of body fluids, and other therapeutic applications.

Figure 1:
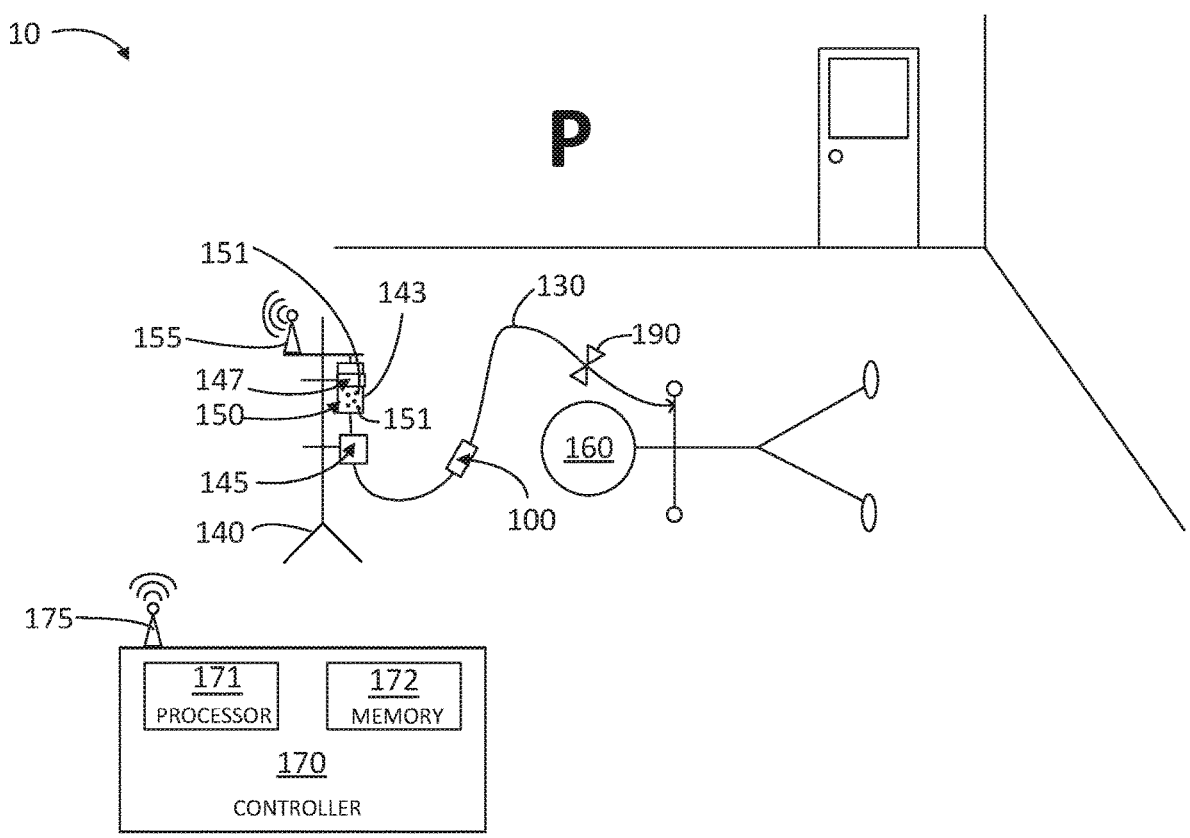
FIG. 1 illustrates a fluid flow system including a sensor to monitor fluid flow, according to some embodiments.

FIG. 1 illustrates a fluid flow system 10 including a sensor 100 to monitor fluid flow, according to some embodiments. Fluid flow system 10 may include a frame 140 supporting a container 143 having a fluid 150. In some embodiments, fluid flow system 10 may include a fluid extraction system to extract a sample fluid from a patient 160. Further, in some embodiments fluid flow system 10 may transfer fluid 150 from a first vessel or container to a second vessel or container, e.g., for medication preparation and or storage purposes.

In some embodiments, fluid flow system 10 is an intravenous delivery system and fluid 150 may include an intravenous fluid to be administered to patient 160 through a blood vessel. Accordingly, fluid 150 may include blood, plasma, or a medication. In some embodiments, fluid 150 includes a gas that may be dissolved, that may be in the form of gas bubbles 151, or that may form a gas phase above a liquid surface, or include any combination of these forms. Gas in gas bubbles 151 may be air, nitrogen, oxygen, or any other gas susceptible of being dissolved in fluid 150. Fluid 150 may be any liquid suitable for intravenous delivery. Common intravenous liquids include crystalloids (e.g., saline, Lactated Ringers, glucose, dextrose), colloids (e.g., hydroxyethyl starch, gelatin), liquid medications, buffer solutions, and blood products (e.g., packed red blood cells, plasma, clotting factors) or blood substitutes (e.g., artificial blood) that are desired to be injected intravenously to a patient 160. A fluid line 130 carries fluid 150 from container 143 to patient 160. In some embodiments, fluid 150 moves through fluid line 130 by a pressure differential created by gravity. Accordingly, in some embodiments container 143 is disposed on frame 140 at a higher elevation relative to the patient. In some embodiments, a pump 145 creates the pressure differential to move liquid 150 through fluid line 130.

Some embodiments of fluid flow system 10 include a thermostat 147 to adjust a temperature of fluid 150 in container 143. The fluid flow system includes a sensor 100 fluidically coupled with fluid line 130. Sensor 100 is configured to provide multiple measurements of the fluid flow. In some embodiments, sensor 100 is configured to measure fluid pressure, fluid flow rate, a bubble concentration, a fluid temperature, and a fluid conductivity of the fluid flow. In some embodiments, sensor 100 is configured to measure a pressure differential between the fluid in fluid delivery system 10, and an atmospheric pressure, P.

In some embodiments, the operation of fluid flow system 10 may be controlled wirelessly by a remote controller 170 located, for example, at a nurse station. The wireless communication may be performed by an antenna 175 on the controller side and an antenna 155 on frame 140. Controller 170 includes a processor 171 and a memory 172. Memory 172 may include commands and instructions, which when executed by processor 171, cause controller 170 to perform at least partially some of the steps included in methods consistent with the present disclosure. Furthermore, sensor 100 may wirelessly communicate with antenna 155 and with controller 170, to receive instructions from and provide data to, controller 170.

Controller 170, antenna 155, and sensor 100 may communicate via a Bluetooth, Wi-Fi, or any other radio-frequency protocol. Accordingly, controller 170 may be configured to process a reading from sensor 100 and determine a fluid flow rate and other characteristics of the fluid relevant for a medication transfer or infusion. A valve 190 in fluid line 130 may be operated to allow fluid 150 to flow into patient 160 when sensor 100 detects a bubble content lower than a predetermined threshold. In some embodiments, valve 190 may be closed by controller 170 when an alarm is issued as described above.

Furthermore, controller 170 may provide an alarm to a centralized system when a bubble count in sensor 100 becomes higher than a threshold. In some embodiments, controller 170 may also provide commands to thermostat 147 to regulate the temperature of fluid 150 based on a bubble count or a temperature measurement provided by sensor 100.

Figure 2:
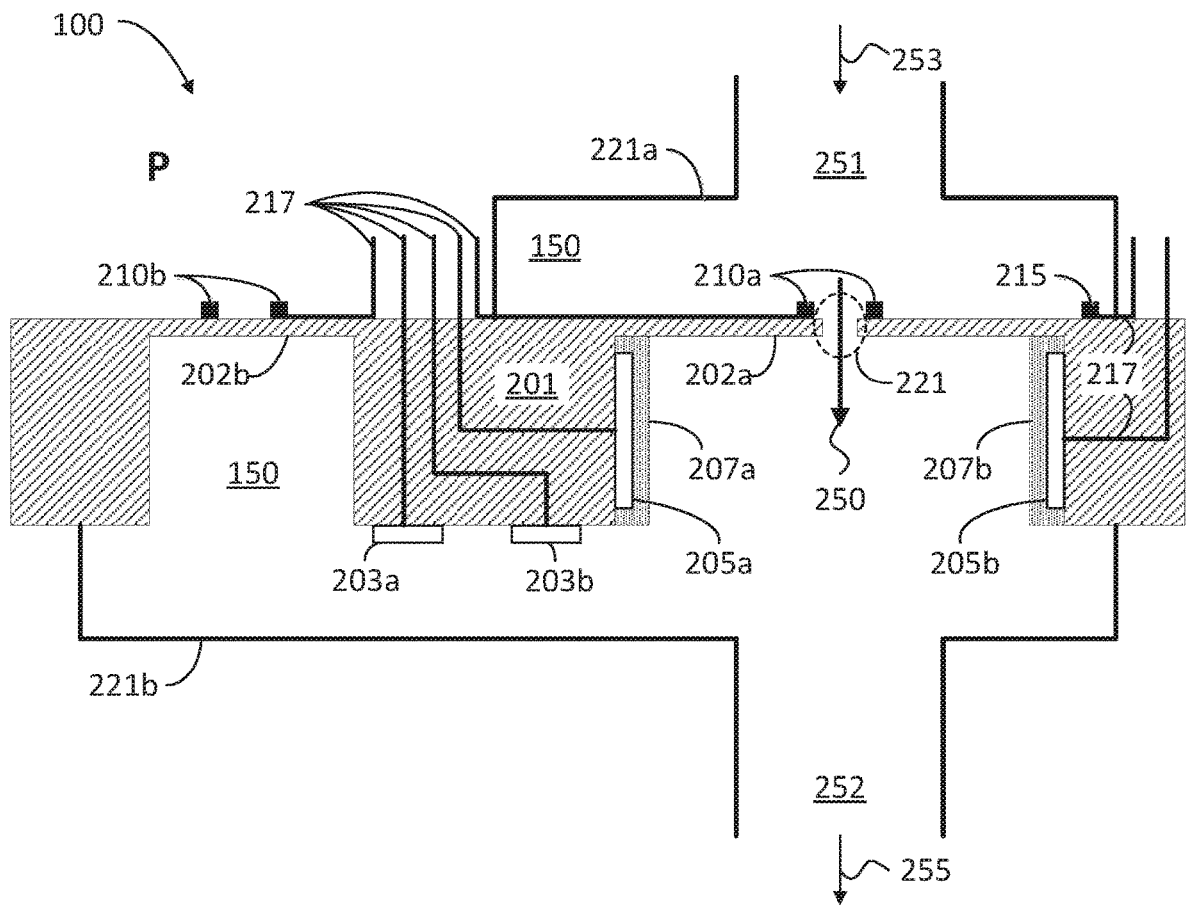
FIG. 2 illustrates a sensor to monitor fluid flow, according to some embodiments.

FIG. 2 illustrates sensor 100 to monitor fluid flow, according to some embodiments. In some embodiments, sensor 100 may use silicon MEMS fabrication technology to incorporate multiple sensing capabilities in a package that has a substantially reduced form factor. For example, and without limitation, some embodiments may include up to five or more sensing modalities, as shown.

Sensor 100 includes an inlet chamber 251 configured to receive a fluid flow 250 from a first conduit 253. An outlet chamber 252 is configured to provide fluid flow 250 to a second conduit 255. A membrane 202a separates inlet chamber 251 from outlet chamber 252. Membrane 202a may include a fluid passage 221 to allow fluid flow 250 from inlet chamber 251 to outlet chamber 252. In some embodiments, membrane 202a may be an epitaxial layer grown over a substrate 201, wherein substrate 201 is thereafter etched on its "backside" (bottom portion in the figure). Accordingly, in some embodiments, fluid passage 221 may be formed by etching an orifice into membrane 202a.

In some embodiments, sensor 100 includes a circuit component 210a disposed on membrane 202a. Circuit component 210a may be configured to change an electrical property according to a deformation of membrane 202a. Some embodiments further include multiple conductors 217 formed on substrate 201 to provide power and receive electric signals from different circuit components in sensor 100. In some embodiments, a conductor 217 provides an electrical signal to circuit component 210a, based on the change in the electrical property of circuit component 210a to a circuit configured to obtain a flow rate for fluid flow 250 using the electrical signal. In some embodiments, membrane 202a is an epitaxial layer formed on the substrate. In some embodiments, a sensing modality in sensor 100 may include a flow rate measurement based on Torricelli's law relating a pressure drop between inlet chamber 251 and outlet chamber 252 across fluid passage 221, to the flow rate.

In some embodiments circuit component 210a is a piezo-resistive element and the electrical property is an electrical resistance. Circuit component 210a is formed in an area proximal and around fluid passage 221 to detect a deformation of membrane 202a, which is related to the pressure difference between inlet chamber 251 and outlet chamber 252. Monitoring circuit component 210a thus gives a direct measure of the pressure drop across membrane 202a, which can be used to calculate the flow rate through fluid passage 221 (e.g., by using Torricelli's law).

Piezo-resistive pressure sensors work on the principle of piezo-resistance, which is the dependence of the conductivity of a material on the strain present in the material. Accordingly, membrane 202a is formed with selectively doped piezo-resistor regions (e.g., circuit component 210a). A pressure difference across membrane 202a causes it to flex (or "buckle") under the applied stress. For example, a pressure difference across membrane 202a is caused by a pressure drop of fluid flow through fluid passage 221. An internal stress generated by a strain or deformation of membrane 202a compensates for the pressure difference. The strain in membrane 202a produces a change in resistance of piezo-resistive elements 210a. The change in resistance may be detected electronically, e.g., with a Wheatstone bridge circuit architecture, accessible through one or more conductors 217.

Some embodiments include a second circuit component 210b disposed on a second membrane 202b. Second membrane 202b separates outlet chamber 252 from an atmospheric pressure, P. Without limitation, some embodiments may include second membrane 202b separating inlet chamber 251 from atmospheric pressure, P. Accordingly, one side of membrane 202b is in contact with fluid 150, and the other side is exposed to atmospheric pressure, P. Thus, membrane 202b is deformed (e.g., "strained") to compensate the pressure differential between fluid 150 (in either of inlet chamber 251 or outlet chamber 252) and atmospheric pressure, P. For example, membrane 202b may "cave in" to outlet chamber 252 when atmospheric pressure, P, is larger than the fluid pressure in outlet chamber 252. On the contrary, membrane 202b may "bulge out" of chamber 252 when atmospheric pressure, P, is lower than the fluid pressure in outlet chamber 252. Membrane 202a and second membrane 202b will be hereinafter collectively referred to as "membranes 202." In some embodiments, second circuit component 210b may be configured to change an electrical property according to the deformation of second membrane 202b. For example, second circuit component 210b may include a piezo-resistive element configured to change its resistivity as it is deformed in compliance with the deformation of second membrane 202b. Hereinafter, circuit component 210a and second circuit component 210b will be collectively referred to as "circuit components 210." Accordingly, a similar principle to the flow rate measurement described above is used to monitor a fluid pressure in one of inlet chamber 251 or outlet chamber 252, relative to atmospheric pressure, P.

In some embodiments, substrate 201 includes a semiconductor material (e.g., silicon, germanium, gallium arsenide, and any combination or alloy of the above, and the like), and membranes 202 include an epitaxial layer grown over the semiconductor material.

Some embodiments further include electrodes 203a and 203b (hereinafter, collectively referred to as "electrodes 203") deposited on substrate 201. Electrodes 203 may be configured to make contact with fluid 150 to measure an electrical property of fluid 150, such as a fluid conductivity. Fluid conductivity is monitored by measuring the impedance between electrodes 203, which are exposed to fluid 150 in a defined geometry (e.g., horizontally along a predetermined distance, as FIG. 2 illustrates). A conductor 217 may provide a current, e.g., a direct-current (DC) to electrodes 203. Accordingly, a DC impedance and a geometric factor yield the fluid conductivity.

Some embodiments further include electrodes 205a and 205b (hereinafter, collectively referred to as "electrodes 205") deposited on the substrate and separated from fluid 150 by passivation layers 207a and 207b, respectively (hereinafter, collectively referred to as "passivation layers 207"). Electrodes 205 may be configured to measure a capacitance of fluid 150, which may be indicative of a dielectric property of fluid 150. In some embodiments, electrodes 205 are configured to measure a bubble content in the fluid through the value of the electrical permittivity, $\varepsilon$, of fluid 150. The capacitance between electrodes 205 may be determined by the dielectric properties of fluid 150. For example, a capacitance may be higher when water or some high permittivity fluid fills the void between electrodes 205, as compared to an air gap with the same geometry, because of the higher permittivity of water. In some embodiments, sensor 100 monitors the capacitance between electrodes 205 as a function of time, so that the presence and size of air bubbles can be detected.

In some embodiments, sensor 100 includes a temperature sensor 215 to measure a fluid temperature. In embodiments including silicon integrated circuits (e.g., MEMS), temperature sensor 215 may include a bandgap sensor, wherein the measurement is based on the variation in voltage of a forward biased diode as a function of the P-N junction temperature. A voltage across temperature sensor 215 may be provided through a conductor 217. In some embodiments, a thin passivating layer is formed over the P-N junction to electrically isolate the diode from the fluid, while still allowing for a thermal equilibrium between the fluid and the P-N junction. Temperature compensation and linearization circuitry can be included on-chip as well.

Alternative arrangements of the components may work equally well; the particular arrangement shown in the drawings is just one potential solution. In one aspect, the monolithic incorporation of five sensing capabilities in a single silicon MEMS chip is highly desirable for a compact, easy to use application.

Sensor 100 may be incorporated into various systems, components, or as a standalone module to be connected in line with the patient's IV access port. For example, it could be incorporated into a micro-pumping device and provide active feedback of the controlled flow rate as well as enable alarm generation should the pressure or fluid conductivity be found out of range or if air is detected in the line. Alternately this low cost sensor could be integrated into a smart catheter, for example, to allow for monitoring of all intravenous fluid delivery to a patient.

FIGS. 3A-G illustrate steps in a method for fabricating an integrated sensor 100 to monitor fluid delivery, according to some embodiments. FIGS. 3A-G illustrate a schematic overview of a method for making sensor 100 using a standard silicon MEMS process, with a cross-section of the device at some of the fabrication steps. The device is built into a single silicon die and then integrated into a housing to provide fluid and electrical connections. For purely illustrative reasons and without loss of generality, the top end of the substrate in FIGS. 3A-G will be referred to as "front" end, and the bottom end of the substrate in FIGS. 3A-G will be referred to as "back" end.

Figure 3A:
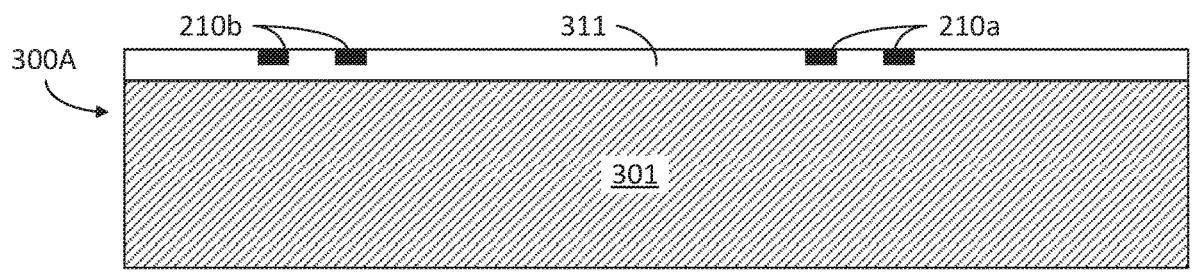
FIGS. 3A-G illustrate steps in a method for fabricating the sensor in FIG. 2 to monitor fluid flow, according to some embodiments.

FIG. 3A illustrates a step 300A, according to some embodiments. In step 300A, a bare silicon wafer 301 has an epitaxial layer 311 grown on the front surface. Dopant atoms are selectively implanted into this epitaxial layer to form the piezo-resistor elements 210. When the substrate material includes a semiconductor such as silicon, the dopant atoms may include electron donor atoms, such as phosphorus (P) or arsenic (As), or electron accepting atoms such as boron (B) or aluminum (Al), or any combination of donor and acceptor atoms. The flexing of the silicon membrane due to pressure differentials across the membranes is detected by the change in resistance of these implanted regions induced by a strain in the crystal lattice.

Figure 3B:
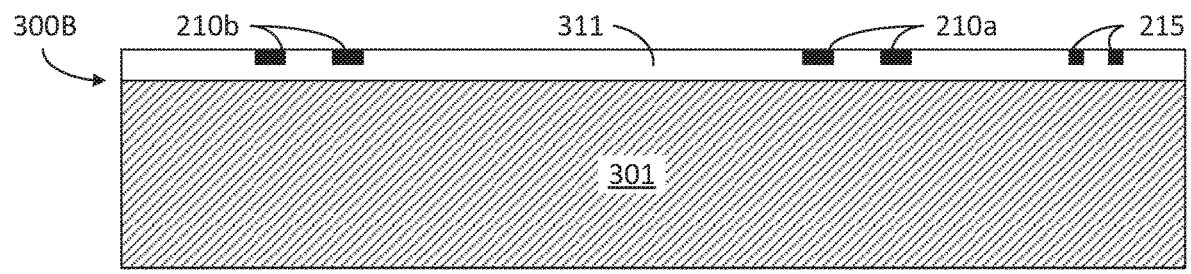

FIG. 3B illustrates a step 300B, according to some embodiments. In step 300B, temperature sensor circuitry 215 is developed on the front side of silicon wafer 301.

Figure 3C:
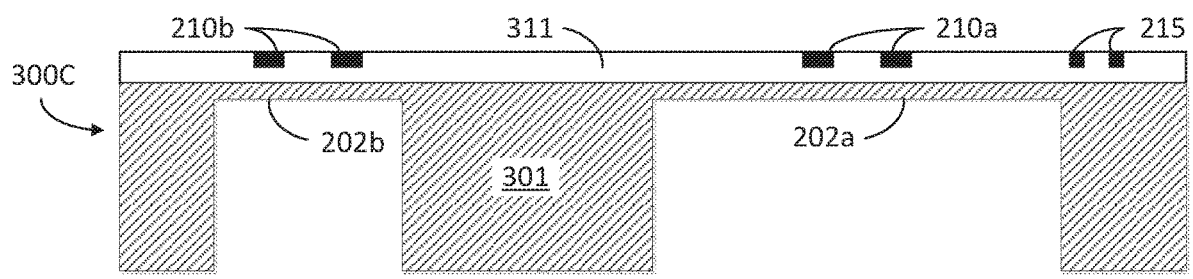

FIG. 3C illustrates a step 300C, according to some embodiments. In step 300C, membranes 202a and 202b are formed by a deep silicon etch from the backside of silicon wafer 301.

Figure 3D:
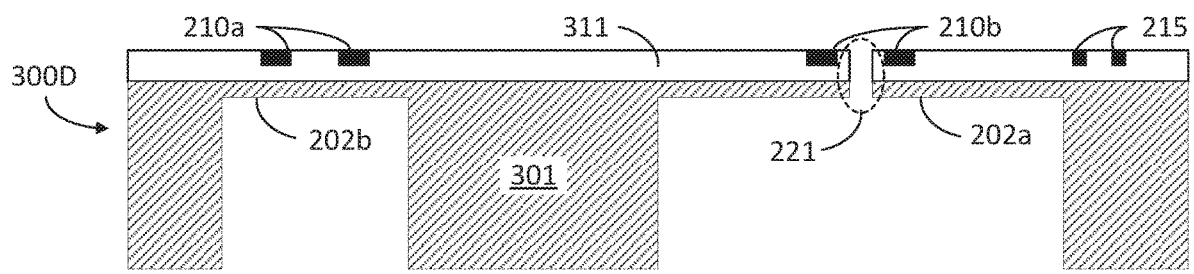

FIG. 3D illustrates a step 300D wherein fluid passage 221 is etched through membrane 202a proximal to piezo-resistive components 210a, according to some embodiments. In step 300D, fluid passage 221 enables fluid flow 250 from the front end to the back end of silicon wafer 301. Once fluid passage 221 is formed in membrane 221, substrate 301 is formed into the shape of substrate 201, described in detail above.

Figure 3E:
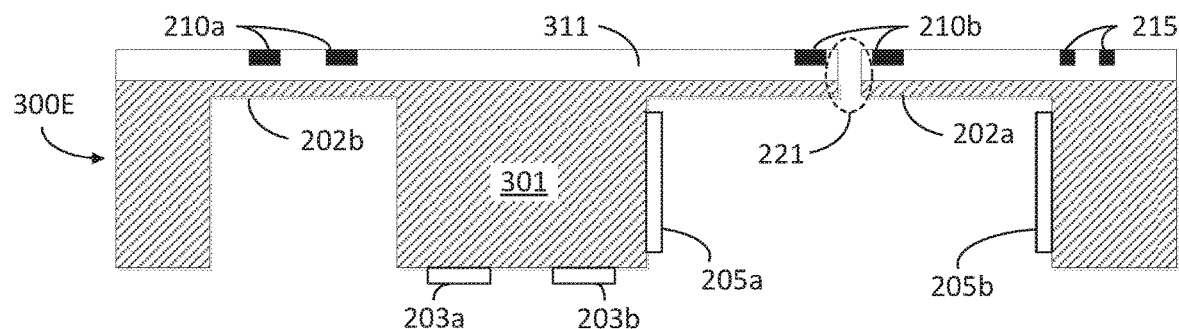

FIG. 3E illustrates a step 300E, according to some embodiments. In step 300E, a backside metallization is performed to form electrodes 203 for a conductivity sensor and electrodes 205 for a capacitive sensor. In some embodiments, this may be accomplished in one step (if both electrodes 203 and electrodes 205 are the same material stack) or in multiple steps. Electrodes 203 and electrodes 205 need not be the same material, as electrodes 203 are exposed to fluid 150, while electrodes 205 are not. Electrodes 205 are deposited on the sidewall of membrane 202a. This could be accomplished through a lift-off procedure, or alternately, the metal could be uniformly deposited and then etched from the surface regions.

Figure 3F:
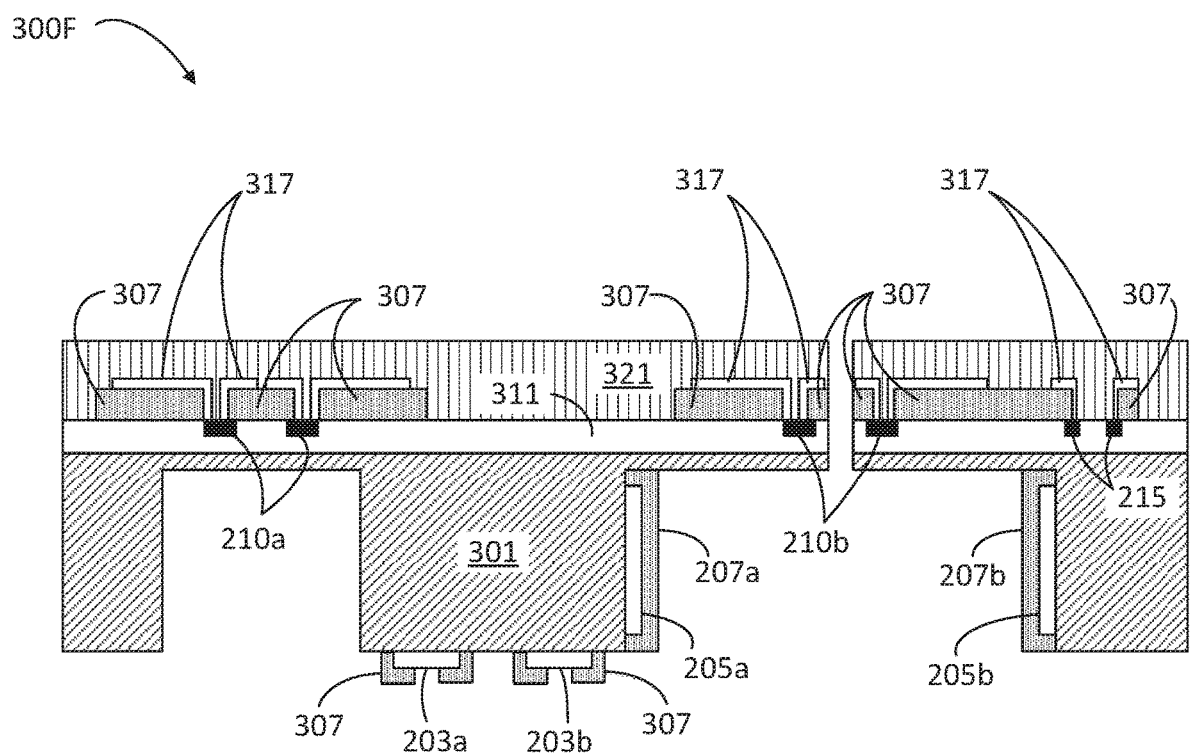

FIG. 3F illustrates a step 300F, according to some embodiments. In step 300F, a passivation layer 307 is deposited on the backside of substrate 201 to isolate electrodes 205 from fluid 150, and selectively etched to open windows to expose electrodes 203 to fluid 150. In some embodiments, in step 300F the front side isolation and metallization is performed to create selective contacts to piezo-resistors 210 for the pressure sensor and the flow rate sensor, and temperature sensor 215.

In some embodiments, step 300F includes passivating the front side of substrate 301 with an additional passivation layer 321 to isolate the electrical components from the fluid path. The passivation material for passivation layers 307 or 321 may include a conformal polymer such as parylene, or an inorganic glass layer such as silicon dioxide.

Figure 3G:
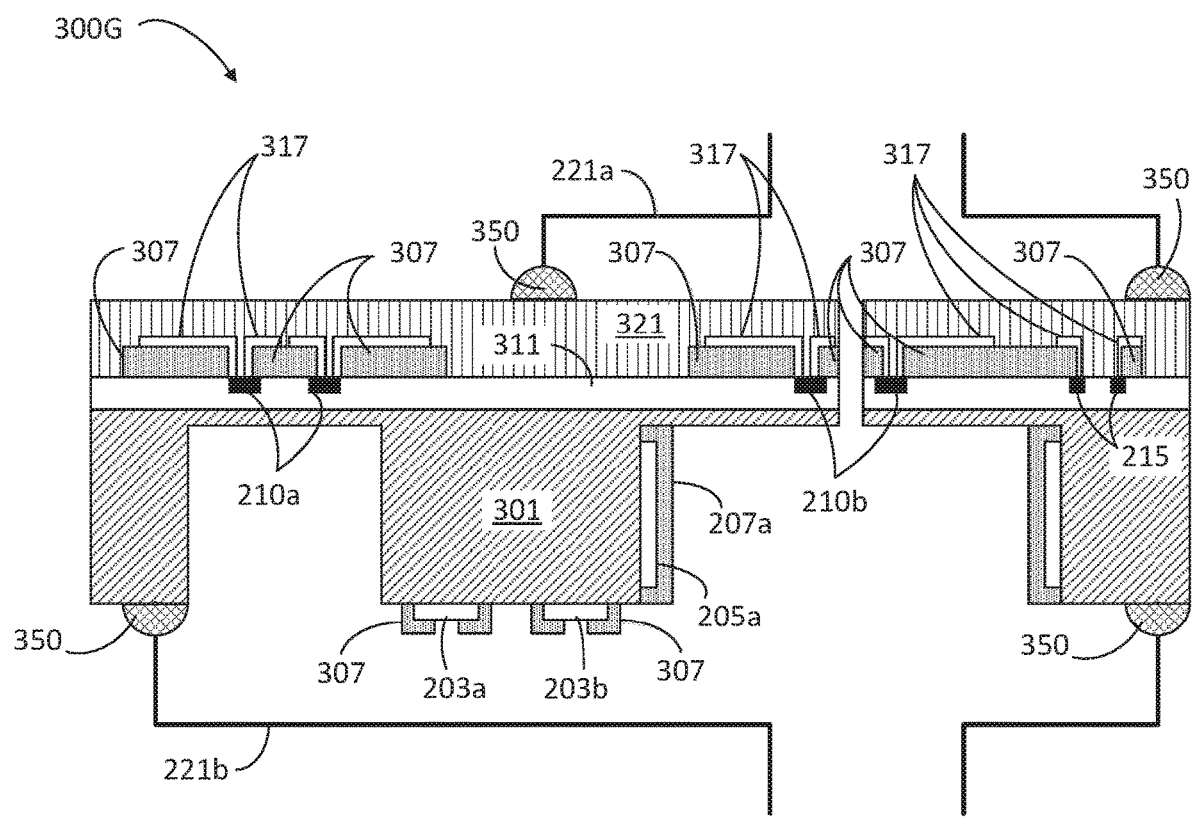

FIG. 3G illustrates a step 300G, according to some embodiments. In some embodiments, in step 300G fittings 221 are attached to the sensor die through adhesive portions 350. In some embodiments, step 300G includes wire bonding to the individual electrodes and final packaging in a housing, to complete the MEMS process.

Figure 4:
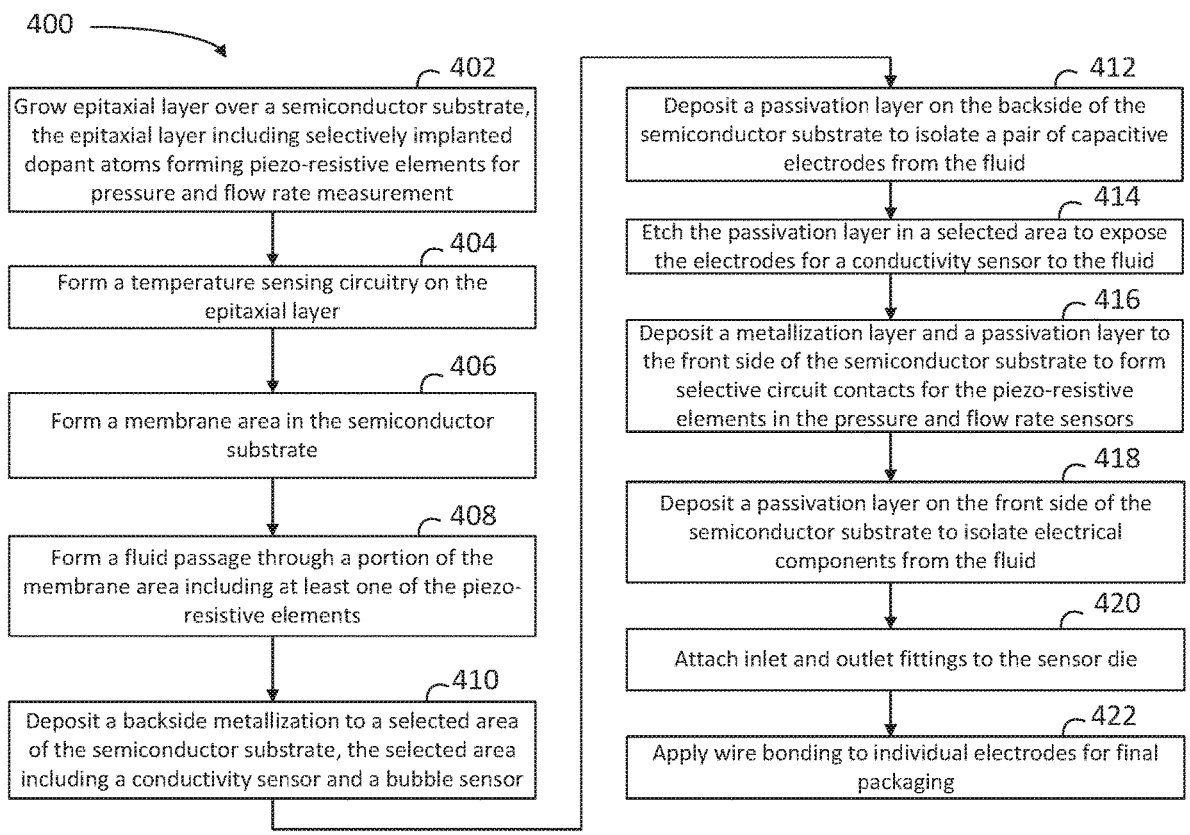
FIG. 4 illustrates a flowchart in a method for fabricating a sensor to monitor fluid flow, according to some embodiments.

FIG. 4 illustrates a flowchart in a method 400 for fabricating an integrated sensor to monitor fluid delivery (e.g., sensor 100), according to some embodiments. Accordingly, in some embodiments method 400 includes forming the sensor on a semiconductor substrate (e.g., substrate 201) using a MEMS configuration. The integrated sensor in method 400 may include multiple components configured to measure fluid properties such as flow rate, pressure, salinity, bubble content, and the like.

Steps in method 400 may be performed overlapping in time, or almost simultaneously. Further, some embodiments, consistent with the present disclosure, may include at least one, but not all, of the steps illustrated in method 400, performed in any order.

Step 402 includes growing an epitaxial layer over a front side of a semiconductor substrate. In some embodiments, step 402 includes selectively implanting a dopant atom to form an electrical component sensitive to a strain in the epitaxial layer. In some embodiments, step 402 includes forming, with the selectively implanted dopant atom, a piezo-resistive element for pressure and flow rate measurement. The piezo-resistive element may have a resistivity that changes according to a strain induced in the epitaxial layer.

Step 404 includes forming a temperature sensing circuitry on the epitaxial layer.

Step 406 includes forming a membrane in the semiconductor substrate. In some embodiments, step 406 may include etching a backside of the semiconductor substrate up to the epitaxial layer formed on the front side. Accordingly, in some embodiments, step 404 includes selecting a thickness of the membrane such that a pressure difference between opposite sides of the membrane (e.g., a front end and a back end) induces a strain in the epitaxial layer.

Step 408 includes forming a fluid passage through a portion of the membrane area including at least one of the piezo-resistive elements. In some embodiments, step 408 includes etching the portion of the membrane to form the fluid passage.

Step 410 includes depositing a backside metallization to a selected area of the semiconductor substrate, the selected area including a conductivity sensor and a bubble sensor.

Step 412 includes depositing a passivation layer on the backside of the semiconductor substrate to isolate a pair of capacitive electrodes from the fluid.

Step 414 includes etching the passivation layer in a selected area to expose the electrodes for a conductivity sensor to the fluid.

Step 416 includes depositing a metallization layer and a passivation layer to the front side of the semiconductor substrate to form selective circuit contacts for the piezo-resistive elements in the pressure and flow rate sensors.

Step 418 includes depositing a passivation layer on the front side of the semiconductor substrate to isolate electrical components from the fluid.

Step 420 includes attaching inlet and outlet fittings to the sensor die to form an inlet chamber and an outlet chamber separated by the membrane (e.g., inlet chamber 251 and outlet chamber 252).

Step 422 includes applying wire bonding to individual electrodes for final packaging.

Figure 5:
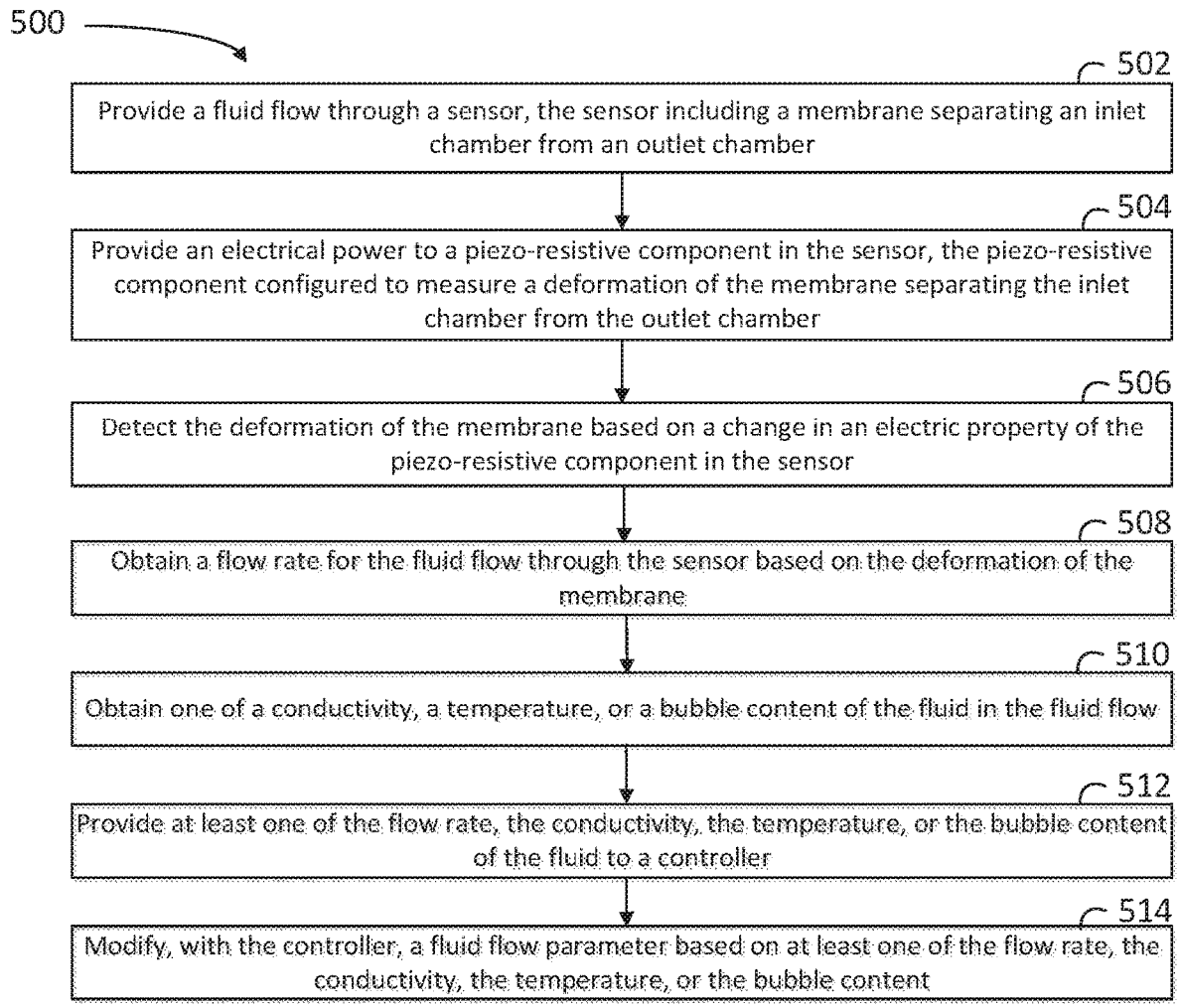
FIG. 5 illustrates a flowchart in a method for monitoring a fluid flow with a sensor, according to some embodiments.

FIG. 5 illustrates a flowchart in a method 500 for monitoring a fluid flow with an integrated sensor, according to some embodiments. Methods consistent with method 500 may include using an integrated sensor as disclosed herein, having at least one measuring component (e.g., integrated sensor 100). Further according to some embodiments, methods consistent with the present disclosure may include an IV delivery system as disclosed herein (e.g., fluid flow system 10). The IV delivery system may include a frame, a fluid container, a pump, a thermostat, a fluid line, an antenna, a sensor, and a valve as disclosed herein (e.g., frame 140, fluid container 143, pump 145, fluid line 130, antenna 155, sensor 100, and valve 190, cf. FIG. 1).

Methods consistent with method 500 may include at least one step in method 500 performed by a controller including a memory and a processor (e.g., controller 170, processor 171, and memory 172, cf. FIG. 1). The memory stores commands, which, when executed by a processor, cause the controller to perform at least one step in method 500. Further according to some embodiments, methods consistent with method 500 may include at least one, but not all, of the steps illustrated in FIG. 5. Moreover, in some embodiments, a method as disclosed herein may include steps in method 500 performed in a different sequence than that illustrated in FIG. 5. For example, in some embodiments, at least two or more of the steps in method 500 may be performed overlapping in time, or even simultaneously, or quasi-simultaneously.

Step 502 includes providing a fluid flow through the sensor, the sensor including a membrane separating an inlet chamber from an outlet chamber (e.g., membrane 202a, inlet chamber 251, outlet chamber 252).

Step 504 includes providing an electrical power to a piezo-resistive component in the sensor, the piezo-resistive component configured to measure a deformation of the membrane separating the inlet chamber from the outlet chamber.

Step 506 includes detecting the deformation of the membrane based on a change in an electric property of the piezo-resistive component in the sensor.

Step 508 includes obtaining a flow rate for the fluid flow through the sensor, based on the deformation of the membrane.

Step 510 includes obtaining one of a conductivity, a temperature, or a bubble content of the fluid in the fluid flow. Step 510 may include performing a DC measurement of impedance between two electrodes (e.g., electrodes 203) with a known geometry relative to a fluid volume. To measure impedance, step 510 may include applying a fixed voltage across the electrodes and measuring the resulting current. In some embodiments, step 510 may include applying a fixed current through the electrodes and measuring the resulting voltage. Step 510 may include selecting between one of the above methods for a conductivity measurement based on the actual conductivity of the fluid. In some embodiments, step 510 may include implementing the above two techniques for measuring conductivity of the fluid in the fluid flow. Based on the measured impedance and a geometric correction factor, the conductivity of the fluid in the fluid flow can be derived. Step 510 may include measuring the temperature of the fluid in the fluid flow with a temperature sensor including a diode having a P-N junction (e.g., temperature sensor 215). Accordingly, step 510 may include applying a fixed current through the diode and measuring a voltage across the junction. The forward voltage across a diode (for a constant current density) is linear with temperature over a wide operating range.

In some embodiments, step 510 may further include measuring a capacitance between a pair of electrodes (e.g., electrodes 205). Accordingly, step 510 may include monitoring the capacitance between the pair of electrodes as a function of time, and detecting the presence and size of air bubbles based on the capacitance values as a function of time.

Step 512 includes providing at least one of the flow rate, the conductivity, the temperature, or the bubble content of the fluid to the controller.

Step 514 includes modifying, with the controller, a fluid flow parameter based on at least one of the flow rate, the conductivity, the temperature, or the bubble content.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (e.g., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method for making a sensor assembly for use in a fluid flow application, the method comprising:
   growing an epitaxial layer on a first side of a substrate, the epitaxial layer comprising a first side and an opposing second side, the second side touching the substrate;
   selectively implanting dopant atoms into the epitaxial layer to form an electrical component disposed at the first side of the epitaxial layer and not touching the substrate, the electrical component sensitive to a strain in the epitaxial layer;
   forming a membrane from a portion of the substrate touching the second side of the epitaxial layer and opposing an entirety of the electrical component, the membrane having a thickness selected so that a pressure difference between opposite sides of the membrane induces the strain in the epitaxial layer;
   forming a fluid passage through the epitaxial layer and the membrane;
   attaching an inlet fitting on the first side of the substrate to form an inlet chamber on a first side of the membrane;
   attaching an outlet fitting to a second side of the substrate to form an outlet chamber on a second side of the membrane;
   bonding an electrical connector to the electrical component;
   forming a temperature sensing component in the epitaxial layer on the first side of the substrate; and
   depositing a metallization layer to a selected area of the substrate, to form a capacitance sensor, wherein the metallization layer is formed as one or more electrodes on a sidewall of the substrate within the outlet chamber, the sidewall disposed between the first and second sides of the substrate.

2. The method of claim 1, wherein the electrical component is formed as one or more piezo-resistor elements.

3. The method of claim 1, wherein the electrical component is disposed on the first side of the membrane within the inlet chamber.

4. The method of claim 1, wherein the electrical connector is a first electrical connector, the method further comprising forming a second electrical connector on the first side of the substrate, the second electrical connector connected to the temperature sensing component.

5. The method of claim 1, wherein the membrane is formed by a deep silicon etch from the second side of the substrate.

6. The method of claim 1, further comprising depositing a metallization layer to a selected area of the substrate, to form a conductivity sensor.

7. The method of claim 6, wherein the metallization layer is formed as one or more electrodes on the second side of the substrate within the outlet chamber.

8. The method of claim 1, further comprising depositing a passivation layer over the metallization layer, the passivation layer separating the metallization layer from fluid in the outlet chamber.

9. The method of claim 1, further comprising depositing a metallization layer and a passivation layer over the membrane to form electrical contacts to the electrical component.

10. The method of claim 1, further comprising depositing a passivation layer on the substrate, and etching the passivation layer in the substrate.

11. The method of claim 1, wherein the membrane is a first membrane, the method further comprising forming a second membrane on the first side of the substrate outside of the inlet chamber, the second membrane separating an atmospheric pressure from the outlet chamber.

12. The method of claim 11, wherein the electrical component is a first electrical component, the method further comprising forming a second electrical component on the second membrane to measure a fluid pressure from a strain in the second membrane.

13. The method of claim 12, further comprising forming a second electrical connector on the first side of the substrate, the second electrical connector connected to the second electrical component.

14. The method of claim 1, further comprising forming a passivation layer on the first side of the substrate to isolate the electrical component from fluid in the inlet chamber.

15. The method of claim 1, wherein the inlet and outlet fittings are attached to the first and second sides of the substrate through adhesive portions.

16. The method of claim 1, further comprising packaging the sensor assembly in a housing.

* * * * *